United States Patent [19]
Dannecker et al.

[11] Patent Number: 5,935,562
[45] Date of Patent: Aug. 10, 1999

[54] PERMANENT PROCESS AND AGENT

[75] Inventors: Beate Dannecker, Darmstadt; Günther Lang, Reinheim; Helmut Keller, Darmstadt; Ulrike Bohr, Ober-Ramstadt, all of Germany

[73] Assignee: Wella AG, Darmstadt, Germany

[21] Appl. No.: 08/930,927

[22] PCT Filed: Dec. 7, 1996

[86] PCT No.: PCT/EP96/05670

§ 371 Date: Oct. 6, 1997

§ 102(e) Date: Oct. 6, 1997

[87] PCT Pub. No.: WO97/32563

PCT Pub. Date: Sep. 12, 1997

[30] Foreign Application Priority Data

Mar. 9, 1996 [DE] Germany .................. 196 08 581

[51] Int. Cl.$^6$ ........................................ A61K 7/06
[52] U.S. Cl. .......................... 424/70.5; 424/70.2
[58] Field of Search .................... 424/70.2, 70.5

[56] References Cited

U.S. PATENT DOCUMENTS 5,338,847  8/1994  McCapra .
5,451,738  9/1995  Teramoto et al. .
5,521,289  5/1996  Hainfeld et al. .

FOREIGN PATENT DOCUMENTS 948 186  8/1956  Germany .
972 424  7/1959  Germany .

*Primary Examiner*—Rebecca Cook
*Attorney, Agent, or Firm*—Michael J. Striker

[57] ABSTRACT

The subject of the invention is a composition and a method for permanent hairwaving, in which 1-thio-β-D-glucose or its salts are used as keratin-reducing active ingredients.

The composition affords a gentle and even shaping of the hair in a skin- and hair protective pH range of 7.0 to 8.5, without causing allergic and sensitizing reactions.

5 Claims, No Drawings

PERMANENT PROCESS AND AGENT

This is a 371 PCT/EP96/05670 filed Dec. 7, 1996.

BACKGROUND OF THE INVENTION

1. Field of the Invention

The present invention relates to a composition for permanent hairwaving containing as a keratin-reducing active ingredient 1-thio-β-D-glucose or its salts, particularly 1-thio-β-D-glucose-ammonium salts or sodium salt dihydrate, as well as a process for permanent hairwaving using this composition.

2. Prior Art

It is known that the customary method for performing permanent hairwaving is based on two treatment steps: in the first step the cystine-disulfide-bridges of the hair keratin are split by the effects of a preparation which contains a reducing substance (waving composition). Then the hair is shaped as desired. In a second step, cystine-disulfide-bonds are closed again through the use of a neutralizer, i.e. a preparation containing an oxidizing active ingredient.

As the pioneering work in German Patent Applications 948 186 and 972 424 shows, thioglycolic acid is used as the classic permanent reduction agent, for example as ammonium or mono-ethanol amine salt. Other conventional active reducing substances are inorganic sulfites, 2-mercapto propionic acid (thiolactic acid); 3-mercapto propionic acid, certain mercapto carboxylic acid esters, cysteine and derivatives of these compounds.

However, all of these solutions have a number of disadvantages. Alkaline adjusted preparations based on thiocarboxylic acid exhibit damage to the hair despite sufficient effects, which for example presents itself in increased cases of hair breakage. Frequently these types of solutions stress the scalp by undesirable reactions. The mercapto carboxylic acid esters, which make hairwaving possible even in the neutral and slightly acidic range, are not satisfactory with regard to their tolerance by the skin and their sensitizing risks.

The use of the thiolactic acid makes it possible to solve some of the problems mentioned. However, thiolactic acid produces a weaker shaping effect than the customarily used thioglycolic acid.

SUMMARY OF THE INVENTION

It is therefore the object of the applicant to make a hairwaving composition available, which satisfactorily produces a permanent wave of the hair in a pH range of 7.0 to 8.5 which is gentle to the skin and to the hair and does not have any physiological disadvantages.

It was now surprisingly discovery that the above mentioned disadvantages can be avoided by using 1-thio-β-D-glucose or its salts, particularly 1-thio-β-D-glucose-sodium salt dihydrate, and that these compounds show a higher shaping potential than thiolactic acid, particularly in a pH range of 7.0 to 8.5.

Therefore, the subject of the instant invention is a composition for permanent hairwaving based on a keratin-reducing active ingredient, which is distinguished in that it contains 1-thio-β-D-glucose or its salts, particularly 1-thio-β-D-glucose sodium salt dihydrate, as the keratin-reducing active ingredient. Ammonium or sodium salt in particular is suitable as the salt, but also any other water-soluble, physiologically tolerated salt with organic and inorganic bases.

The 1-thio-β-D-glucose or its salts should preferably be contained in the ready-to-use composition for permanent hairwaving in an amount of 3 to 28 weight-percent and most preferred in an amount of 5 to 21 weight-percent.

The ready-to-use hairwaving composition has a pH value of 7 to 8.5, preferably 7.5 to 8.5, wherein as a rule alkalizing can be achieved by adding ammonium hydrogen carbonate, besides ammonia.

The composition preferably contains 1-thio-β-D-glucose or its salts as the sole keratin-reducing active ingredient. However, it can also be used in combination with other keratin-reducing active ingredients, for example thioglycolic acid, thiolactic acid, 2-hydroxy-3-mercapto propionic acid, cysteamine and cysteamine derivatives or cysteine and cysteine derivatives, for example cysteine-(2-hydroxy ethyl)-ester or L-cysteine-glycerine ester.

The shaping composition can be prepared in the form of a one-, two- or three-component preparation, wherein the composition can either be present in form of an aqueous solution or an emulsion, or in a thickened water-based form, particularly as a cream, gel or paste.

For example, the composition in accordance with the invention can be obtained by mixing two components, of which the first component contains at least one alkalizing agent, for example an alkali carbonate, ammonium carbonate, alkali hydrogen carbonate or ammonium hydrogen carbonate and 1-thio-β-D-glucose or its salts, and the second component contains at least one of the cosmetic additives mentioned below and water.

It is also possible to package the permanent hairwaving composition in form of a three-component preparation, wherein one component contains some of the cosmetic additives mentioned below, as well as water, a second, non-aqueous component contains 1-thio-β-D-glucose or its salts, and the third component further additives, such as perfume oils, solubilizers and care substances, in an aqueous solution or in non-aqueous form.

In all embodiments of the composition in accordance with the invention, the cosmetic additives can be contained in the aqueous as well as the non-aqueous component(s).

It is understood that the waving composition can contain all additives commonly known and used for such preparations, for example thickeners, such a bentonite, fatty acids of higher alcohols, starch, polyacrylic acid and its derivatives, cellulose derivatives, alginates, vaseline, paraffin oils, wetting agents or emulsifiers from the category of anionic, cationic, amphoteric or non-ionogenic surfactants, for example fatty alcohol sulfates, fatty alcohol ether sulfates, alkyl sulfonates, alkyl benzene sulfates, quaternary ammonium salts, alkyl betaines, ethoxylated alkyl phenols, fatty acid alkanolamides or ethoxylated fatty acid esters; in addition opacifiers, for example polyethylene glycol ester; alcohols, such as ethyl alcohol, propyl alcohol, isopropyl alcohol and glycerin; sugar such as D-glucose; solubilizers, stabilizers, buffer substances, perfume oils, pigments as well as hair-conditioning and hair care components, such as cationic polymers, lanolin derivatives, cholesterol, pantothenic acid and betaine.

The components referred to are used in the appropriate quantity commonly employed for these purposes, for example the wetting agents and emulsifiers in concentrations of 0.2 to 30 weight-percent in total, the alcohols in a quantity of 0.1 to 20 weight-percent in total, the opacifiers, perfume oils and pigments in a quantity of 0.01 to 1 weight-percent each, the buffer substances in a quantity of 0.1 to 10 weight-percent in total, sugar, solubilizers, stabilizers, as well as hair-conditioning and hair care components in a quantity of 0.1 to 5 weight-percent each, while the thickeners and solubilizers can be contained in this preparation in a quantity of 0.5 to 20 weight-percent in total.

For increased strength, so-called swelling and penetration substances, for example dipropylene glycol monomethyl ether, 2-pyrrolidone or 2-imidazolidinone, in a quantity of 2 to 30 weight-percent, as well as dithio compounds, for example dithiodiglycolic acid, dithiolactic acid or its salts for the prevention of excessive frizzing of the hair, can also be added to this preparation.

By varying the pH value, a composition can be made available, which is universally suitable for every hair structure, if necessary with the additional use of heat. The composition creates an elastic, permanent and even wave starting at the hairline and extending to the tip of the hair, without causing allergic or sensitizing reactions.

Further the present invention relates to a method for permanent hairwaving, in which the hair prior and/or after the desired form has been set, is treated with a waving composition, rinsed with water, then treated oxidatively, rinsed with water and if necessary set as water-wave and then dried, which is distinguished in that the above mentioned solutions in accordance with the invention are used as waving composition.

In a preferred embodiment of the process in accordance with the invention the hair is first washed with a shampoo and then rinsed with water. Subsequently the towel-dried hair is divided into single strands and rolled on rollers of a diameter of 5 to 30 millimeters, preferably 5 to 15 millimeters. For the hairwaving, the hair then is treated with a sufficient amount, preferably 60 to 120 grams, of the described waving composition in accordance with the invention.

After a sufficient reaction time necessary for the permanent shaping which takes, depending on the nature of the hair, the pH value and the shaping action of the waving composition, as well the temperature used, 5 to 30 minutes (10 to 30 minutes without heat application; 5 to 20 minutes with heat application), the hair is rinsed with water and then oxidatively treated ("neutralized"). The post-treatment agent is used, depending on the fullness of the hair, preferably in amounts between 80 and 100 grams.

For the oxidative post-treatment in the rolled or unrolled state, any arbitrary post-treatment preparation appropriate for such a treatment can be used. Examples of oxidizing agents usable in such post-treatment preparations are potassium- and sodium bromate, sodium perborate, carbamide peroxide and hydrogen peroxide. The concentration of the oxidizing agent differs, depending on the usage time (as a rule 5 to 15 minutes) and the temperature in use. Normally the oxidizing agent in the ready-to-use aqueous post-treatment preparation is present at a concentration of 0.5 to 10 weight-percent. Of course, the preparation for the oxidative post-treatment can contain additional substances, for example wetting agents, care substances, such as cationic polymers, weak acids, buffer substances or peroxide stabilizers, and can be present in form of an aqueous solution, an emulsion, as well as in a thickened water-based form, particularly as a cream, gel or paste. These conventional additives can be present in a post-treatment preparation particularly in a quantity of 0.1 to 10 weight-percent.

If necessary, the unrolled hair can now receive another oxidative post-treatment. Subsequently the hair is rinsed with water, if need be set in a water-wave and then finally dried.

The following examples are intended to explain the subject of the invention in more detail, however, without limiting the object to these examples.

EXAMPLES

Example 1

Comparison of the Wave Strengths

The wave strength of 1-thio-β-D-glucose sodium salt-dihydrate was determined by using glycerine monothioglycolate as comparative substance with the aid of wave solutions at pH=7, 8 and 9. To this end, pre-bleached and therefore damaged, counted hair strands, 16.5 centimeters long (consisting of approx. 100 hairs) of central European origin, were rolled in wet condition on standard spiral rollers (interior diameter: 3 millimeters) and after conditioning in a climate controlled room (temperature: 20° C.; humidity: 65%) were treated with a solution containing 87 mmol/100 g of the reduction preparation, set to the respective pH value. The amount of the waving solution applied was calculated at a ratio of 1:1.2 (1 g hair: 1.2 ml waving solution). The reaction time was selected to be 20 minutes; the reaction temperature was 50° Celsius. Subsequently the hair was neutralized with a neutralizer containing peroxide, dried, and after unrolling was suspended for four hours into a water bath (water bath temperature: 40° C.).

The wave stability was calculated in accordance with the following formula:

$$\text{Wave Stability in } \% : \frac{l_o - l_t}{l_o - l_1} \times 100$$

$l_o$=total length of the non-shaped, stretched strands (16.5 cm)

$l_t$=length of the unrolled, suspended strand after 240 minutes $l_1$=length of the shaped, rolled strands
with an interior roller diameter of 3 millimeters: $l_1$=35 millimeters As the standard, small strands were treated with a glycerine monothioglycolate solution, set correspondingly to a pH of 9. The standardized wave stabilities listed in Table I refer to this standard solution (pH=9), whose wave stability was set to 100 percent.

TABLE I

Standardized Wave Stability (WSN) in %.

| pH of Wave Solution | WSN of Thiolactic Acid | WSN of 1-Thio-β-D-Glucose-Sodium Salt-Dihydrate |
|---|---|---|
| 7 | 57% | 63% |
| 8 | 50% | 63% |
| 9 | 70% | 59% |

Table I shows, that the wave strength of 1-thio-μ-D-glucose sodium salt dihydrate is higher at pH 7 and pH 8 than with thiolactic acid.

Example 2

Permanent Hairwaving Composition for Colored Hair

| | |
|---|---|
| 12.0 g | 1-thio-β-D-glucose-sodium salt dihydrate |
| 0.4 g | Ammonia, (25% aqueous solution) |
| 2.0 g | Ammonium hydrogen carbonate |

-continued

| | |
|---|---|
| 2.0 g | Isopropanol |
| 1.0 g | Isooctylphenol, ethoxylated with 1.0 mol ethylene oxide |
| 1.0 g | Polydimethyl diallylammonium chloride |
| 0.3 g | Perfume oil |
| 0.1 g | Mixed vinyl pyrrolidon/styrol polymer (Antara<sup>R</sup> 430 of GAF Corp; New York/USA) |
| 81.2 g | Water |
| 100.0 g | |

The pH value of this composition lies in the range between 7.0–7.5.

Color treated and therefore pre-damaged hair is washed with a shampoo, towel-dried and rolled onto rollers with a diameter of 8 millimeters. Subsequently, the previously described hairwaving composition is evenly applied over the rolled hair. Then the hair is covered with a plastic cap and is warmed for 10 minutes under a dryer at a temperature of 65° Celsius. Subsequently the cover is removed, the hair is rinsed with water and receives an oxidative post-treatment with 100 grams of a 3-percent aqueous hydrogen peroxide solution. After removal of the rollers the hair is once again rinsed in water, set in a water-wave and then dried.

This treatment results in an even, elastic and permanent shaping of the hair.

Example 3

Permanent Hairwaving Composition for Normal Hair

| | |
|---|---|
| 17.5 g | 1-thio-β-D-sodium salt dihydrate |
| 8.9 g | Ammonia (25% aqueous solution) |
| 5.0 g | Ammonium hydrogen carbonate |
| 2.0 g | D-gluaose |
| 2.4 g | Ammonia |
| 1.5 g | Isooatylphenol, ethoxylated with 10 mol ethylene oxide |
| 0.5 g | Polydimethyl diallylammonium chloride |
| 0.5 g | Perfume oil |
| 0.1 g | Mixed vinyl pyrrolidon/styrol polymer (Antara<sup>(R)</sup> 430 of GAF Corp; New York/USA) |
| 61.6 g | Water |
| 100.0 g | |

The pH value of this composition lies in the range between 8.0–8.5.

Normal, not previously damaged hair is washed, towel-dried and rolled onto rollers 6 millimeters in diameter. Subsequently the hair is evenly moisturized with the previously described hairwaving composition. After a reaction time of 15–25 minutes the hair is thoroughly rinsed in water and then receives an oxidative post-treatment with 80 grams of a 3-percent aqueous hydrogen peroxide solution. After removal of the rollers the hair is once again rinsed in water, set in a water-wave and then dried.

The thus treated hair has an even and lively frizz.

We claim:

1. A composition for permanent hair waving having a pH of from 7.0 to 8.5 and comprising from 3 to 28 percent by weight of 1-thio-β-D-glucose or a salt thereof as keratin reducing substance; and from 0.2 to 30 percent by weight of at least one cosmetic additive ingredient selected from the group consisting of thickeners, anionic surfactants, cationic surfactants, amphoteric surfactants, non-ionogenic surfactants, opacifiers, alcohols, sugars, solubilizers, stabilizers, buffer substances, perfume oils, pigments and hair care substances.

2. The composition as defined in claim 1, wherein the at least one cosmetic additive ingredient are buffer substances comprising a mixture comprising alkali carbonate and alkali hydrogen carbonate or a mixture comprising ammonia, ammonium carbonate and ammonium hydrogen carbonate.

3. A method for permanent hairwaving of hair, said method comprising the steps of:

a) providing a composition having a pH of from 7.0 to 8.5 and comprising from 3 to 28 percent by weight of 1-thio-β-D-glucose or a salt thereof as keratin reducing substance;

b) setting the hair in a desired shape;

c) before or after step b), applying to the hair a sufficient amount of said composition provided in step a) for the permanent hairwaving;

d) leaving said amount of said composition on the hair for a time interval sufficient for the permanent hairwaving;

e) rinsing the composition from the hair with water after step d);

f) oxidatively post-treating the hair after step e).

4. The method as defined in claim 3, wherein said amount of said composition applied to the hair is from 60 to 120 grams.

5. The method as defined in claim 3, wherein said time interval is from 5 to 30 minutes without heat application or from 5 to 20 minutes with heat application.

* * * * *